US007593763B2

United States Patent
Lambert et al.

(10) Patent No.: US 7,593,763 B2
(45) Date of Patent: Sep. 22, 2009

(54) NON-INVASIVE IN VIVO MEASUREMENT OF MACULAR CAROTENOIDS

(75) Inventors: James L. Lambert, Sunland, CA (US); Mark S. Borchert, La Canada, CA (US)

(73) Assignees: Childrens Hospital Los Angeles, Los Angeles, CA (US); California Institute of Technology, Pasadena, CA (US)

( * ) Notice: Subject to any disclaimer, the term of this patent is extended or adjusted under 35 U.S.C. 154(b) by 898 days.

(21) Appl. No.: 10/773,099

(22) Filed: Feb. 5, 2004

(65) Prior Publication Data

US 2004/0260183 A1    Dec. 23, 2004

Related U.S. Application Data

(60) Provisional application No. 60/445,046, filed on Feb. 5, 2003.

(51) Int. Cl.
    *A61B 6/00* (2006.01)
(52) U.S. Cl. ....................... 600/476; 600/473
(58) Field of Classification Search ................. 600/424, 600/476–9; 356/479, 497
    See application file for complete search history.

(56) References Cited

U.S. PATENT DOCUMENTS

| 5,873,831 | A | 2/1999 | Bernstein et al. ............ 600/473 |
| 6,002,480 | A | 12/1999 | Izatt et al. .................... 356/479 |
| 6,014,214 | A * | 1/2000 | Li ................................ 356/511 |
| 6,205,354 | B1 | 3/2001 | Gellerman et al. .......... 600/477 |
| 6,608,684 | B1 | 8/2003 | Gelikonov et al. .......... 356/479 |
| 6,725,073 | B1 * | 4/2004 | Motamedi et al. ........... 600/316 |
| 7,039,452 | B2 * | 5/2006 | McClane et al. ............. 600/424 |
| 7,061,622 | B2 * | 6/2006 | Rollins et al. ............... 356/497 |
| 2003/0072007 | A1 | 4/2003 | Fercher ...................... 356/497 |

FOREIGN PATENT DOCUMENTS

| WO | 99/29229 | 6/1999 |
| WO | 03/058200 | 7/2003 |

OTHER PUBLICATIONS

"Assessing Carotenoid Content in Plant Leaves with Reflectance Spectroscopy" Photochemistry and Photobiology, 2002, 75(3): 272-281.*
Gellermann et al., "In vivo resonant Raman measurement of macular carotenoid pigments in the young and aging human retina", J. Opt. Soc. Am. A/vol. 19, No. 6, Jun. 2002, pp. 1172-1186.
Morgner et al., "Spectroscopic optical coherence tomography", Optic Letters, vol. 25, No. 2, Jan. 15, 2000, pp. 111-113.

(Continued)

*Primary Examiner*—Eric F Winakur
*Assistant Examiner*—Michael T Rozanski
(74) *Attorney, Agent, or Firm*—Myers Bigel Sibley & Sajovec

(57) ABSTRACT

A non-invasive in vivo method for assessing macular carotenoids includes performing Optical Coherence Tomography (OCT) on a retina of a subject. A spatial representation of carotenoid levels in the macula based on data from the OCT of the retina can be generated.

26 Claims, 7 Drawing Sheets

OTHER PUBLICATIONS

Mitne et al., "Agreement between optical coherence tomography and fundus fluorescein angiography in post-cataract surgery cystoid macular edema", Arq Bras Oftalmol 2003; 66:771-4.

New and Emerging Technology Briefing; Optical coherence tomography for the diagnosis of eye disorders, National Horizon Scanning Centre, Jul. 2002.

Gellermann et al., "Raman imaging of human macular pigments", Optics Letters, vol. 27, No. 10, May 15, 2002, pp. 833-835.

Hee et al., "Quantative assessment of macular edema with optical coherence tomography", Arch Ophtalmol. Aug. 1995; 113(8): 1019-29. (abstract).

International Search Report for PCT/US2004/003321.

* cited by examiner

NON-INVASIVE IN VIVO MEASUREMENT OF MACULAR CAROTENOIDS

RELATED APPLICATION

This application claims the benefit of priority to U.S. Provisional Patent Application Ser. No. 60/445,046, entitled "Non-Invasive Measurement of Macular Carotenoids", filed Feb. 5, 2003, the contents of which are hereby incorporated by reference as if recited in full herein.

The invention described herein was made by an agency of the United States Government or under a contract with an agency of the United States Government, namely in the performance of work awarded by NASA under contract number NAS7-1407, and is subject to the provisions of Public Law 96-517 (35 USC § 202) in which the Contractor has elected to retain title. The United States Government has certain rights to this invention.

FIELD OF THE INVENTION

The present invention concerns methods and apparatus for non-invasively measuring or assessing the presence or absence of selected substances in the eye.

BACKGROUND OF THE INVENTION

Age related Macular Degeneration (AMD) is thought to be the leading cause of blindness in the elderly. It has been estimated that about 12 million people in the United States suffer from AMD. Macular carotenoid pigments, such as lutein and zeaxanthin, may play a role in the progression and/or onset of AMD. Carotenoids are from a family of natural pigments that are found in both plants and animals. Animals generally derive carotenoids from dietary sources such as green leafy vegetables and orange and yellow fruits and vegetables. Epidemiological studies have shown that there is an inverse correlation between high dietary intakes of carotenoids and blood levels of lutein and zeaxanthin and the risk of advance AMD. See Eye Disease Case Control Study Group, "Antioxidant status and neovascular age-related macular degeneration," Arch. Ophthalmol (Chicago) 111, 104-109 (1993); J. M. Seddon, U. A. Ajani, R. D. Sperduto, R. Hiller, N. Blair, T. C. Burton, M. D. Farber, E. S. Gragoudas, J. Haller, D. T. Miller, L. A. Yannuzzi, and W. Willet, "Dietary carotenoids, vitamins A, C, and E, and advanced age-related macular degeneration," J.Am. Med. Assoc. 272, 1413-1420 (1994).

It has been hypothesized that carotenoids may protect against AMD because of their free-radical-scavenging properties as antioxidants. The ocular tissue may be at high risk of oxidative damage because of high levels of light exposure. Carotenoids absorb light in the blue-green spectral range; therefore, carotenoids may act as filters that can attenuate photo-chemical damage and/or image degradation caused by short-wavelength visible light reaching the retina. See W. Gellerman; I. V. Ermakov, M. R. Ermakova, R. W. McClane; D. Y. Zhao, and P. S. Bernstein, "In vivo resonant Raman measurements of macular carotenoid pigments in the young and the aging human retina," J. Opt. Soc. Am. A, 19, 6, 1172-1186 (2002).

Raman spectroscopy has been used to obtain spectra indicative of carotenoid pigments in the retina. See Id.; W. Gellerman; I. V. Ermakov, R. W. McClane, P. S. Bernstein, "Raman imaging of human macular pigments," Optics Letters, 27, 10, 833-835 (2002). Lutein and zeaxanthin and other carotenoid pigments feature a Raman-active, π-electron conjugated carbon backbone with alternating carbon-carbon double (C═C) and single (C—C) bonds and strong electronic absorptions. Studies by these researchers reportedly used resonance Raman spectroscopy for the measurement of macular carotenoid levels in excised human eyecups from cadavers (Optics Letters 27, 10, 833-835 (2002)) and in living humans (J. Opt. Soc. Am. A. 19, 6, 1172-1186 (2002)). These studies reported a decline in the Raman signal correlated with increasing age. Id at 1183.

Despite the foregoing, there is a need for improved systems, methods, and devices for the non-invasive in vivo analysis of carotenoids in the eye.

SUMMARY OF THE INVENTION

According to embodiments of the present invention, a non-invasive in vivo method for assessing carotenoids and/or retinoids in the macula and/or retina is provided. Optical Coherence Tomography (OCT) can be performed on a retina of a subject. A spatial representation of carotenoid levels in the retina based on data from the OCT of the retina can be generated.

In some embodiments, OCT can be performed by transmitting a blue excitation light to the retina. In other embodiments, an excitation light is transmitted that includes at least a blue excitation light and an infrared excitation light. The blue and/or infrared light can be a low coherence light transmitted with a superluminescent diode. In particular embodiments, a wavelet transformation can be applied to the OCT signal to generate spectral data of the retina. An absorption and/or reflectance spectrum of the retina can be obtained from the OCT, and carotenoid absorption levels can be identified therein.

In some embodiments, the performing and generating steps can be repeated after the administration of a selected treatment to a subject to provide first and second spatial representations of the carotenoids of the retina. The treatment or different types of treatment can be evaluated based on the change of carotenoid levels in the retina. The first spatial representation can be compared with the second spatial representation and the efficacy of the selected treatment for AMD can be evaluated based on the comparison.

For example, carotenoids can include, but are not limited to, β-carotene, lutein, lycopene, xanthophyl, xanthophyll, and zeaxanthin. The carotenoids can have a chemical structure having at least one double carbon-carbon bonds and/or a single carbon-carbon bond. A detected light spectrum from the OCT can be compared to a priori reference spectra corresponding to different concentrations of a plurality of different concentrations of the carotenoids. In some embodiments, a retinoid concentration in the retina can also be determined. In other embodiments, a resonant Raman spectra can be detected based on the OCT data. In other embodiments, a relative increase or decrease can be determined using at least two OCT scans taken over a desired timeframe.

The OCT scan can be performed by scanning the retina with low coherence light of an OCT scanner, detecting reemitted light from the retina in response thereto, interfering the detected light from the retina with a reference light beam to provide an interference signal, and obtaining a light spectrum from the interference signal.

In some embodiments reflectance and/or absorption spectra of a plurality of different layers of the retina can be detected. The plurality of different layers can include at least seven layers. A two-dimensional map, or, typically, a three-dimensional morphology map of carotenoid level in a cross-sectional spatial representation of the retina can be generated from the OCT, for example, using amplitude and spectral data of absorption and/or reflectance spectra from the OCT.

The spatial representation can be a map of a plurality of adjacent layers of the retina and covers a region that may be between about 2-5 mm wide. The spatial representation can be presented with at least about 1000 pixels. Intensity graduated and/or color indexed images of different levels of carotenoids in the retina can be generated. Age-related macular degeneration (AMD) can be assessed based on the two- or three-dimensional spatial representation of the carotenoid levels.

In some embodiments, a combination of resonant Raman data and OCT data can be obtained to assess the carotenoid levels in the retina. For example, a portion of the retina can be illuminated with an optical excitation beam having a wavelength selected to generate a resonant Raman spectrum of at least one of the carotenoids. A resonant Raman spectrum corresponding to the selected illuminated region of the eye can be detected. Resonant Raman data can be combined with OCT data to generate the more precise level of chemical concentration for a spatial representation of carotenoid levels in the retina. The retina can be illuminated with the optical excitation beam and the OCT data can be generated substantially simultaneously. An OCT signal can be detected and the resonant Raman spectrum can be filtered from the OCT signal.

In some embodiments, a system for providing non-invasive in vivo assessment of macular carotenoids includes an OCT scanner configured to generate an OCT scan of the retina. The OCT scan can include chemical spectra and/or physical structures data of the eye. A carotenoid mapping module is in communication with the OCT scanner and is configured for generating a spatial representation of carotenoid levels in the retina based on data obtained from the OCT scanner. In some embodiments, the OCT scanner can include a blue excitation light source and/or an infrared light source. The carotenoid mapping module can be configured to apply a wavelet transformation to an OCT signal from the OCT scanner to generate spectral data of the retina.

In some embodiments, the system can include a Raman excitation source having a wavelength selected to generate a resonant Raman spectrum of at least one of the carotenoids. A Raman spectrometer can be configured to receive the resonant Raman spectrum. The carotenoid mapping module can be configured to combine resonant Raman spectrum with OCT data from the OCT scanner to generate a spatial representation of carotenoid levels in the retina.

In some embodiments, a minimally invasive in vivo method for assessing carotenoids in tissue of interest is provided. An OCT is performed on selected tissue of interest in and/or on a subject, and a spatial representation of carotenoid levels in the selected tissue is generated based on data from the OCT of the region. The tissue of interest can include internal organs, such as the bladder or prostate.

In other embodiments, a non-invasive in vivo method for assessing retinoids in the retina and/or macula is provided. An Optical Coherence Tomography (OCT) is performed on a retina of a subject. A spatial representation of retinoid levels in the retina is generated based on data from the OCT of the retina.

Numerous additional features may be incorporated into the apparatus. The device may include a visual display screen for presenting visual indicia to the user, which can be individually adjusted and focused to the particular visual acuity of the subject (similar to vision screening focusing procedures). The apparatus may include a visual display screen for visually displaying the results of the test to the subject and/or clinician (such as through the same aperture or adjacent active matrix screen) as which the test is conducted. It may include a visual fixation target or device, also visible through the test aperture, which controls movement of the eye and simultaneously insures that focusing of the OCT beam is properly directed into the retina of the eye.

DESCRIPTION OF EMBODIMENTS OF THE INVENTION

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, layers, components, or features may be exaggerated for clarity and broken lines indicate optional features or operations unless described otherwise.

The term "subject," according to the present invention, includes subjects belonging to the animal kingdom, and are preferably mammalian subjects (e.g., humans, canines, felines, bovines, caprines, ovines, equines, rodents, porcines, and/or lagomorphs), and more preferably are human subjects.

In some embodiments according to the invention, at least one Optical Coherence Tomography (OCT) scan can be used to provide a spatial representation of carotenoid and/or retinoid levels that may be present in the macula or other portions of the retina. Although embodiments of the present invention are described herein with reference to carotenoid levels, it should be understood that some embodiments of the present invention may be used to provide a spatial representation of retinoid levels. In addition, although discussed primarily with respect to OCT mapping of the retina, carotenoids or other target regions/tissues in the body can be assessed according to embodiments of the present invention.

Figure 2:
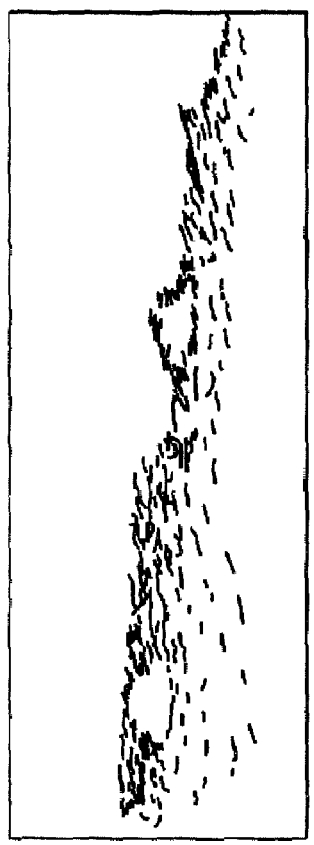
FIG. 2 is a schematic of a cross sectional slice taken from the scan line 2-2 from the image of FIG. 1.
Figure 1:
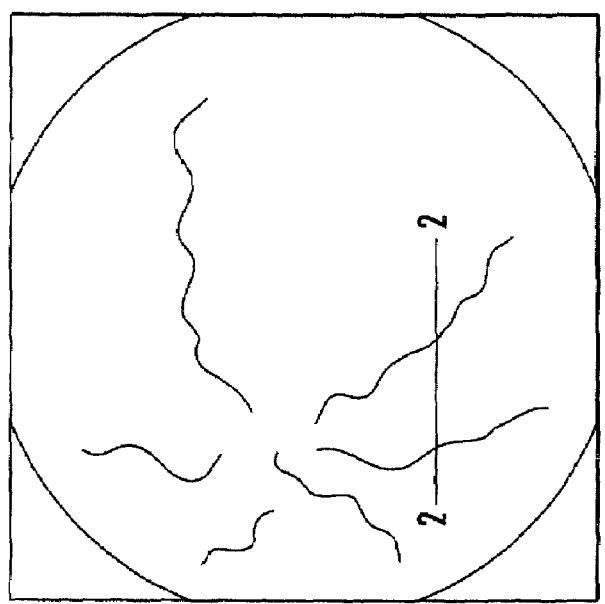
FIG. 1 is a schematic of an image of an eye with a selected target OCT scan line 2-2.

FIG. 1 is a schematic illustrating a typical fundus angiogram of a subject. FIG. 2 is a cross sectional schematic of an image taken along line 2-2 in FIG. 1. As illustrated, areas of low reflectivity are represented by a higher concentration of markings. However, OCT scans typically use color or grey scale drawings to represent the level of reflectivity/absorption. Images of fundus angiograms and OCT images are described in "Optical Coherence Tomography of Ocular Diseases" by Carmen A. Puliafito, Michael R. Hee, Joel S. Schuman, James G. Fujimoto (Slack, Inc. 1996). AMD can cause blood vessels in the eye to leak, which can be observed clinically using a fundus fluorescein angiogram. This leakage can lead to blindness.

OCT techniques have been used to provide noninvasive, cross-sectional optical imaging in biological media. Conventional OCT devices may use a low coherent light source (e.g., a low coherent infrared diode) and an optical interferometer, such as a Michelson optical fiber interferometer, to image tissue as is known to those of skill in the art. Various OCT techniques are described, for example, in U.S. Pat. No. 6,002,480 to Izatt et al. and U.S. Pat. No. 6,608,684 to Gelikonov et al., the disclosures of which are incorporated herein by reference in their entireties. These OCT techniques can generate images, such as the image shown in FIG. 2, such that areas of high reflectivity are represented by lighter shades than areas of low reflectivity. Color images can also be generated such that various levels of reflectivity are assigned to certain colors.

According to embodiments of the present invention, an excitation light can be transmitted to the macular pigment in an OCT scan to generate absorption and/or reflectance spectra. The absorption and/or reflectance can be used to identify the presence and/or intensity of absorption and/or reflectance spectra associated with carotenoids, such as β-carotene, lutein, lycopene, xanthophyl, xanthophyll, and/or zeaxanthin, and to generate a spatial representation of the identified carotenoid levels. A blue excitation light may be used to generate absorption and/or reflectance spectra and/or imaging information. It should be understood that the absorption spectrum may be measured indirectly. For example, a reflectance spectrum can be used to generate an absorption spectrum. The blue light spectra wavelengths may coincide with the absorption spectra of carotenoids. A blue excitation wavelength can also be used in addition to a red or infrared excitation light. As used herein, "infrared" includes near-infrared light. In some embodiments, an OCT scan can be combined with a Raman spectrum. A spatial representation of carotenoid levels can be generated by combining the detected Raman spectrum and OCT data, for example, by "overlaying" a detected Raman spectrum on an OCT image. Examples of Raman spectroscopy devices can be found, for example, in U.S. Pat. No. 6,574,501, the disclosure of which is hereby incorporated by reference in its entirety.

Figure 3:
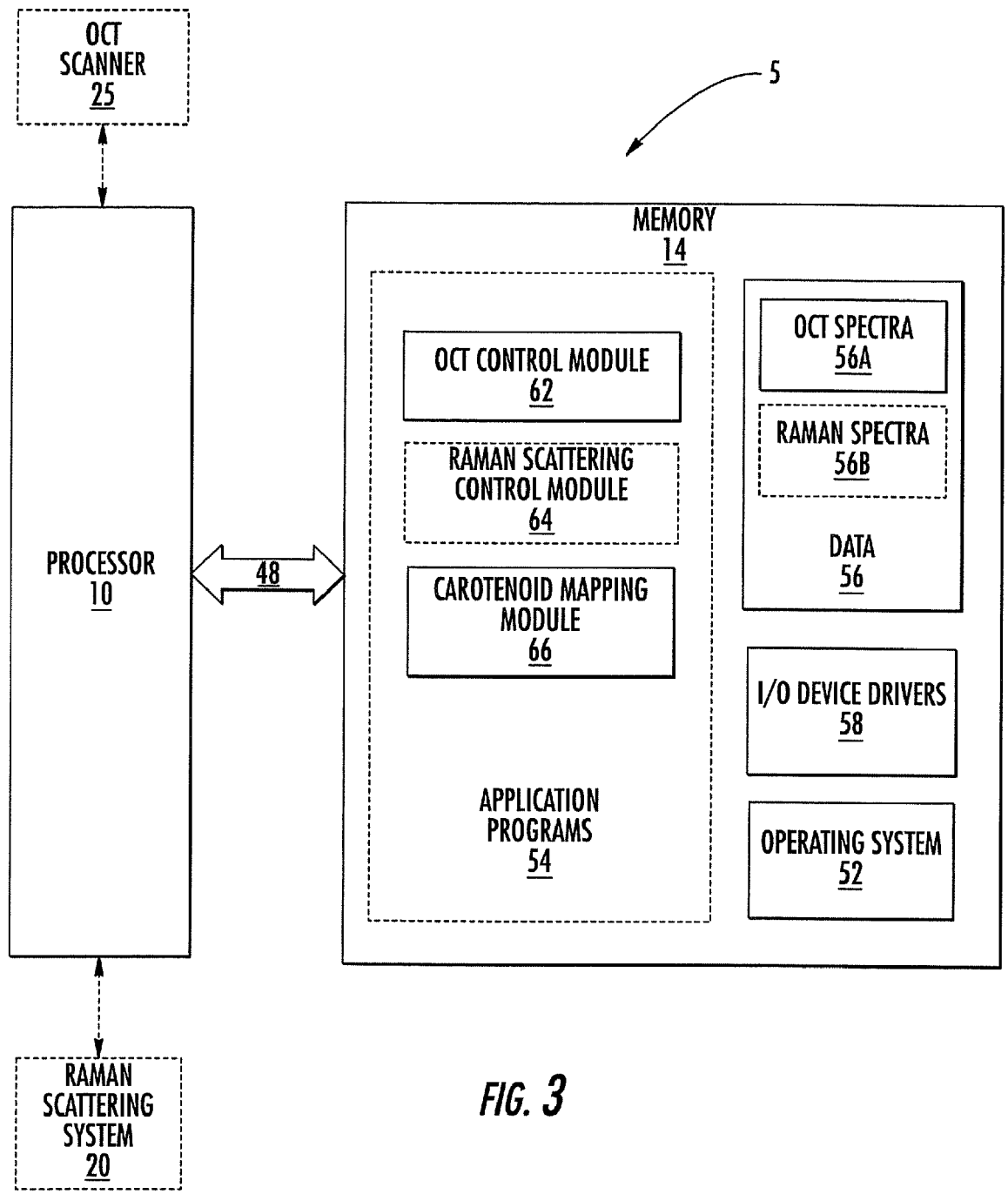
FIG. 3 is a schematic diagram of a data processing system according to embodiments of the present invention.

FIG. 3 is a block diagram of exemplary embodiments of data processing systems that illustrates systems, methods, and computer program products in accordance with embodiments of the present invention. A data processing system 5 includes a processor 10 that can send and receive information to and/or from an OCT scanner 25 and, optionally, in certain embodiments, a Raman scattering system 20. The data processing system 5, Raman scattering system 20 (where used) and/or the OCT scanner 25 may be implemented noninvasively to scan the retina of a subject. It should be understood that the OCT scanner 25 and/or the optional Raman scattering system 20 and/or the data processing system 5 may also be used to perform OCT and (optionally) Raman scattering of other biological tissues, including the prostate and/or the bladder. The data processing system 5, the Raman scattering system 20 and/or the OCT scanner 25 can be provided as separate components or two or more systems or system components can be provided as an integrated system.

As illustrated, the processor 10 communicates with the memory 14 via an address/data bus 48. The processor 10 can be any commercially available or custom microprocessor. The memory 14 is representative of the overall hierarchy of memory devices containing the software and data used to implement the functionality of the data processing system 5. The memory 14 can include, but is not limited to, the following types of devices: cache, ROM, PROM, EPROM, EEPROM, flash memory, SRAM, and DRAM. The memory 14 may include several categories of software and data used in the data processing system 5: an operating system 52; application programs 54; input/output (I/O) device drivers 58; and data 56.

As will be appreciated by those of skill in the art, the operating system 52 may be any operating system suitable for use with a data processing system, such as OS/2, AIX, OS/390 or System390 from International Business Machines Corporation, Armonk, N.Y., Windows CE, Windows NT, Windows95, Windows98, Windows2000 or WindowsXP from Microsoft Corporation, Redmond, Wash., Unix or Linux or FreeBSD, Palm OS from Palm, Inc., Mac OS from Apple Computer, or proprietary operating systems. The I/O device drivers 58 typically include software routines accessed through the operating system 52 by the application programs 54 to communicate with devices such as I/O data port(s), data 56 and certain components of memory 14 components and, optionally, where used, the Raman scattering system 20 or the OCT scanner 25. The application programs 54 are illustrative of the programs that implement the various features of the data processing system 5 and preferably include at least one application which supports operations according to embodiments of the present invention. The data 56 represents the static and dynamic data used by the application programs 54, the operating system 52, the I/O device drivers 58, and other software programs that may reside in the memory 14. The data 56 may include OCT spectra data 56A, such as spectra obtained from the OCT scanner 25 and, optionally, a record of Raman spectra data 56B generated by the Raman scattering system 20.

As shown in FIG. 3, the application programs 54 can include an OCT control module 62, a carotenoid mapping module 66, and, optionally, Raman spectrometer control module 64. The OCT control module 62 can control the operation of the OCT scanner 25. Data from the OCT scanner 25 can be stored as OCT spectra 56A in the data 56. The optional Raman spectrometer control module 64 can control the operation of the Raman scattering system 20, and data from the Raman scattering system 20 can be stored in the Raman spectra 56B. The carotenoid mapping module 66 can generate a spatial representation of carotenoid levels that may be present in the macula based on the OCT data of the macula, and, in certain particular embodiments, based on both the OCT data and the resonant Raman data.

For example, OCT spectra obtained from the OCT scanner 25 and stored in OCT spectra data 56A can be used by the carotenoid mapping module 66 to represent a spatial distribution of carotenoid levels in the macula using detected absorption and/or reflectance spectra. The carotenoid mapping module 66 can apply a Morlet wavelet transformation to an OCT signal to generate spectral data of the macula or other portions of the retina. Phase information can also be obtained. The carotenoid mapping module 66 can also use intensity levels of the OCT signal, for example, to obtain structural information.

Examples of the Morlet wavelet transformation are discussed in U. Morger, W. Drexler, F. X. Kärtner, X. D. Li, C. Pitris, E. P. Ippen, and J. G. Fujimoto, "Spectroscopic Optical Coherence Tomography," 25, 2, Optics Letters, 111-113 (1999), the disclosure of which is hereby incorporated by reference in its entirety. The Morlet wavelet transformation can be mathematically expressed as follows:

$$W(\Omega, \tau) = \left| \int I_D(t+\tau) \exp[-(t/t_0)^2] \exp(i\Omega t) dt \right|^2 \quad \text{Equation (1)}$$

$$= |F\{I_D(t+\tau) \exp[(-t/t_0)^2]\}|^2$$

The above equation can be used to calculate an entire spectrum $W(\Omega)$ for each point $(x,\tau)$ in an OCT image, where x is the distance in the transverse direction, $t_0$ is an initial time, t is a subsequent time, F is a Fourier transform, $I_D$ is the oscillating output from interference of the signal field with a Doppler-shifted reference field from an OCT image scan, and "$\tau$" corresponds to detected light that is reemitted from a corresponding depth z inside the tissue (i.e., such that light from the reference path with a length $z=_g\tau$ scanned continuously at a speed $_g$ is interfered with light from the sample). Examples of configurations that can be used to obtain an OCT scan, including the detection of reemitted light from a sample and a reference path, are discussed further below.

Other transformations to obtain spectral data can also be used, such as Fourier transforms and/or other wavelet transformations. Other computational methods can also be used to characterize the absorption/reflectance spectra to obtain carotenoid levels. For example, ratios of wavelengths in a spectrum can be examined to determine carotenoid levels. Chemometric and/or ratiometric techniques, including pulsed oximetry techniques, can also be used, such as pulsed oximetry techniques described in U.S. Pat. No. 5,351,685, the disclosure of which is hereby incorporated by reference in its entirety. Chemometric techniques are described in "Chemometric Techniques for Quantitative Analysis" by Richard Kramer (Marcel Dekker, 1998). In some embodiments, a portion of the peripheral retina, e.g., outside the macula, can be scanned as a reference baseline for comparison with macular carotenoid levels. Carotenoid levels are generally higher inside the macula or fovea.

In some embodiments, an entire spectrum can be calculated for each point in the OCT image. In certain embodiments, the OCT scanner 25 can use a blue superluminescent diode to generate the excitation light signal to the eye. Ultrashort (femtosecond) pulsed light sources may also be used. Without wishing to be bound by any particular theory, carotenoids generally absorb blue light. Therefore, a blue excitation light may increase sensitivity to the absorption and/or reflectance spectra for carotenoids. Although blue light may produce optimum absorption of retinal carotenoids, it may also have lower penetration into the retina compared to infrared light. Depending on the concentration and/or depth at which the carotenoids are likely to be found, somewhat longer wavelength excitation light may be utilized. In other embodiments, the OCT scanner 25 can use a combination of light bands, such as a blue light band and an infrared light band. The blue light can be a low coherence light having a wavelength range between about 450 nm and about 550 nm and the infrared light can include near infrared light and be a low coherence light source having a wavelength range between about 700 and about 1000 nm. The low coherence light of the OCT scanner 25 can be spatially coherent and spectrally incoherent. In some embodiments, a pulsed (femtosecond) laser light source can be used.

As another example, the carotenoid mapping module 62 can combine OCT spectra data 56A and Raman spectra data 56B to provide a spatial representation of carotenoid levels. The OCT spectra data 56A can be used to generate a morphology or image of the macula or other parts of the retina with associated carotenoid (and/or retinoid) levels, and the Raman spectra data 56B can provide spectra that can be used to identify the presence and/or concentration of carotenoids in a region of the macula or other parts of the retina. The Raman spectra data 56B can be obtained using an excitation beam selected to generate a resonant Raman spectrum for at least one of the carotenoids in the retina. The Raman excitation beam can be a high coherence light. The excitation wavelength can be chosen to induce resonant or pre-resonant Raman scattering of the macular carotenoids using a wavelength between about 400 and 530 nm. As used herein, "resonant" scattering includes "pre-resonant" or "strongly pre-resonant" Raman scattering. Signal enhancements may allow the observation of concentrations of macular carotenoids in the nanogram of carotenoid per milligram of retina at these wavelengths. However, significant absorption at these wavelengths may reduce the ability to examine carotenoids in deeper layers of the retina. Excitation wavelengths of longer wavelengths between 530 nm and 600 nm can be utilized to induce pre-resonant Raman scattering of the macular carotenoids. This can produce a signal enhancement of at least 10 or 1000 times over Raman scattering of macular carotenoids using non-resonant excitation wavelengths while providing deeper penetration into the macula or other parts of the retina. In some embodiments, several millimeters of retinal layers may be observed.

The OCT spectra data 56A can be obtained by the OCT scanner 25 using a low coherence excitation light while the Raman spectra data 56B can be obtained using a high coherence excitation light, such as a laser; however, Raman spectra may also be generated using a low coherence light. In some embodiments, the Raman spectra can be generated using the OCT light source, such as a low coherence blue or infrared diode.

The system 5 can be used to generate a spatial representation of carotenoid levels present in the retina of a subject. In certain embodiments, the actual signal of the subject can then be compared to the stored "signature" profiles or signals of OCT data and/or Raman data corresponding to predetermined carotenoids or carotenoid levels to identify the presence of one or a plurality of the selected carotenoids and/or to estimate or quantitatively determine the concentration of that substance(s) in the retina of the eye of the subject. Thus, the present invention is able to assess, non-invasively, at physiologic levels, the presence of carotenoids in the retina of the subject and to generate a spatial representation of the carotenoid levels in two- or three-dimensions. For example, carotenoids are conjugated polyenes and can have a chemical structure having at least one, and more typically, a series of alternating double carbon-carbon bonds and single carbon-carbon bonds. The OCT spectra (or, optionally, the resonant Raman spectra) may include peaks associated with the single carbon-carbon bond or the double carbon-carbon bond of the chemical structure. The OCT light spectra obtained from the OCT scanner 25 can be compared to a priori reference spectra corresponding to different concentrations of carotenoids.

In some embodiments, reflectance and/or absorption spectra of different layers of the macula or other parts of the retina can be collected, such as about three or four to about seven or eight or more layers of cross sectional spatial representations of carotenoid levels. A two-dimensional map or a three-dimensional map can be generated of carotenoid levels, for example, using amplitude and spectral data of absorption and/or reflectance spectra from the OCT scanner 25. For example, a linear scan across the retina can consist, for example, of 256 pixels across the retina and 100 pixels in depth resolution, providing a 25600 pixel cross-sectional image. Typical pixel resolutions across the retina range from 50 to 1000 pixels. Depth resolution typically ranges from 10 to 250 pixels. The penetration depth of an OCT scan may be about 3 mm for nontransparent tissues. The spatial representation of carotenoid levels can include intensity graduated and/or color indexed images of different levels of carotenoids in the retina.

The spatial representations of carotenoid levels can be used in assessing AMD. For example, epidemiological studies and/or correlations between the spatial representations of carotenoid levels and AMD can be used to assess overall eye health and/or AMD. The efficacy of various types of treatment can also be assessed. Spatial representations of carotenoid levels in the retina can be obtained before and/or after a treatment is administered. Monitoring carotenoid levels before and/or after treatment can assess whether a treatment has affected the carotenoid levels. Treatments that may be assessed in this manner include dietary changes, such as carotenoids administered by vitamin supplements, eye drops, or pharmacological agents or analytes, surgeries, exercise or other interventional treatments. The systems and methods of the present invention may also be used to evaluate, adjust and/or identify therapies in drug/treatment development programs and/or in clinical or pre-clinical drug trials or other drug development testing, including clinical or pre-clinical trials for developing or evaluating vitamin supplements, herbal remedies, and/or other treatments. Embodiments of the present invention may also be used to evaluate, adjust and/or identify a suitable dose of a selected treatment based on the carotenoid levels in the eye.

Although the present invention is illustrated in FIG. 3, for example, with reference to the OCT control module 62, the optional Raman spectrometer control module 64, and the carotenoid mapping module 66 as examples of application programs 54 in FIG. 3, as will be appreciated by those of skill in the art, other configurations may also be utilized. For example, the OCT control module 62, the optional Raman scattering control module 64, and/or the carotenoid mapping module 66 may also be incorporated into the operating system 52, the I/O device drivers 58 or other such logical division of the data processing system 5. Thus, the present invention should not be construed as limited to the configuration of FIG. 3, which is intended to encompass any configuration capable of carrying out the operations described herein.

The I/O device drivers 58 can be used to transfer information between the data processing system 5 and the Raman scattering system 20, the OCT scanner 25, or another computer system or a local or global network (e.g., the Internet) or to other devices controlled by the processor. These components may be conventional components such as those used in many conventional data processing systems that may be configured in accordance with the present invention to operate as described herein.

Figure 4:
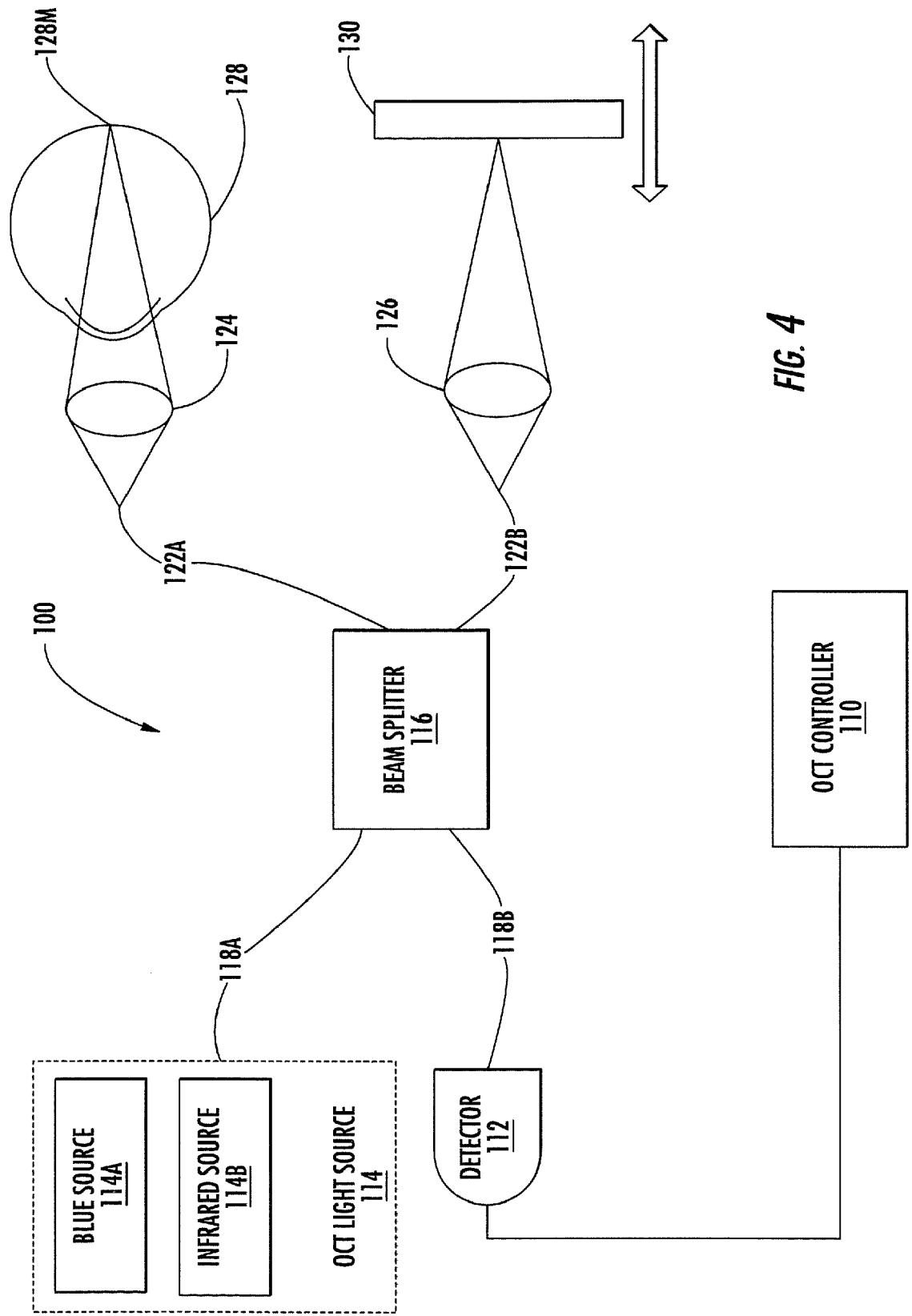
FIG. 4 is a schematic diagram of an OCT device for measuring carotenoids in vivo according to embodiments of the present invention.

An exemplary OCT scanning system 100 is shown in FIG. 4. A light excitation source 114 provides an excitation light to a beam splitter 116 via a fiber optic cable 118A. The beam splitter 116 outputs a scanning excitation light beam on one output fiber optic cable 122A and a reference beam on another fiber optic cable 122B. The scanning and reference beams are transmitted through lenses 124 and 126, respectively. The scanning beam is transmitted to the macula 128M of the eye 128 and can be moved in a transverse direction to scan a cross sectional area of the eye 128. The reference beam is transmitted to a reference mirror 130, which can be moved away from or toward the lens 126. The reemitted light from the reference mirror 130 and the eye 128 are transmitted along fiber optic cables 122A and 122B, respectively, through the beam splitter 116 and to a detector 112. An OCT controller 110 analyzes and interferes the resulting signals. The depth positions of the reemitting locations in the eye 128 can be measured by changing the position of the reference mirror 130 with respect to the lens 126. Thus, a cross sectional OCT scan can be measured at various layers of depth within the eye 128.

As illustrated in FIG. 4, the light excitation source 114 includes a superluminescent blue light source 114A and, optionally, an infrared light source 114B. The OCT scanning system 100 can use the blue light source 114A and/or the infrared light source 114B to provide a light excitation beam. The blue light source 114A and/or the infrared light source 114B can be superluminescent diodes. Because carotenoids generally absorb blue light, the blue light source 114A may be used to provide an absorption and/or reflectance spectrum that is sensitive in the blue range of the light spectrum and/or imaging information. The infrared wavelengths may provide increased depth penetration while the blue wavelengths may provide increased sensitivity to the carotenoid levels. Alternatively, the infrared signal may be used to mask or reduce any visual irritation that a subject may experience from a blue excitation light alone. An interference signal from the infrared light source 114B may provide additional information for imaging the carotenoid levels and/or an absorption and/or reflectance spectrum.

The blue light source 114A and the infrared light source 114B can provide excitation beams in their respective wavelength ranges to the fiber optic cable 118A simultaneously. As would be understood by those of skill in the art, if excitation light beams are used from the blue light source 114A and the infrared light source 114B at the same time, the detector 112 and/or the controller 110 can filter the resulting reemitted light from the reference mirror 130 and the eye 128 to simultaneously analyze the interference spectrum associated with the blue light source 114A and the infrared light source 114B. Thus, two light spectra can be obtained from a single OCT scan using the two light sources 114A, 114B. Alternatively, the infrared source 114B can be used to mask the blue light and the resulting spectra can be disregarded.

Alternatively, an OCT scan can be performed using only the blue light source 114A and a separate OCT scan can be performed using only the infrared light source 114B. As another example, either the blue light source 114A or the infrared light source 114B can be omitted from the OCT scanning system 100.

The operations discussed with respect to the data processing system 5 in FIG. 3 can be incorporated into the OCT controller 110.

Figure 5A:
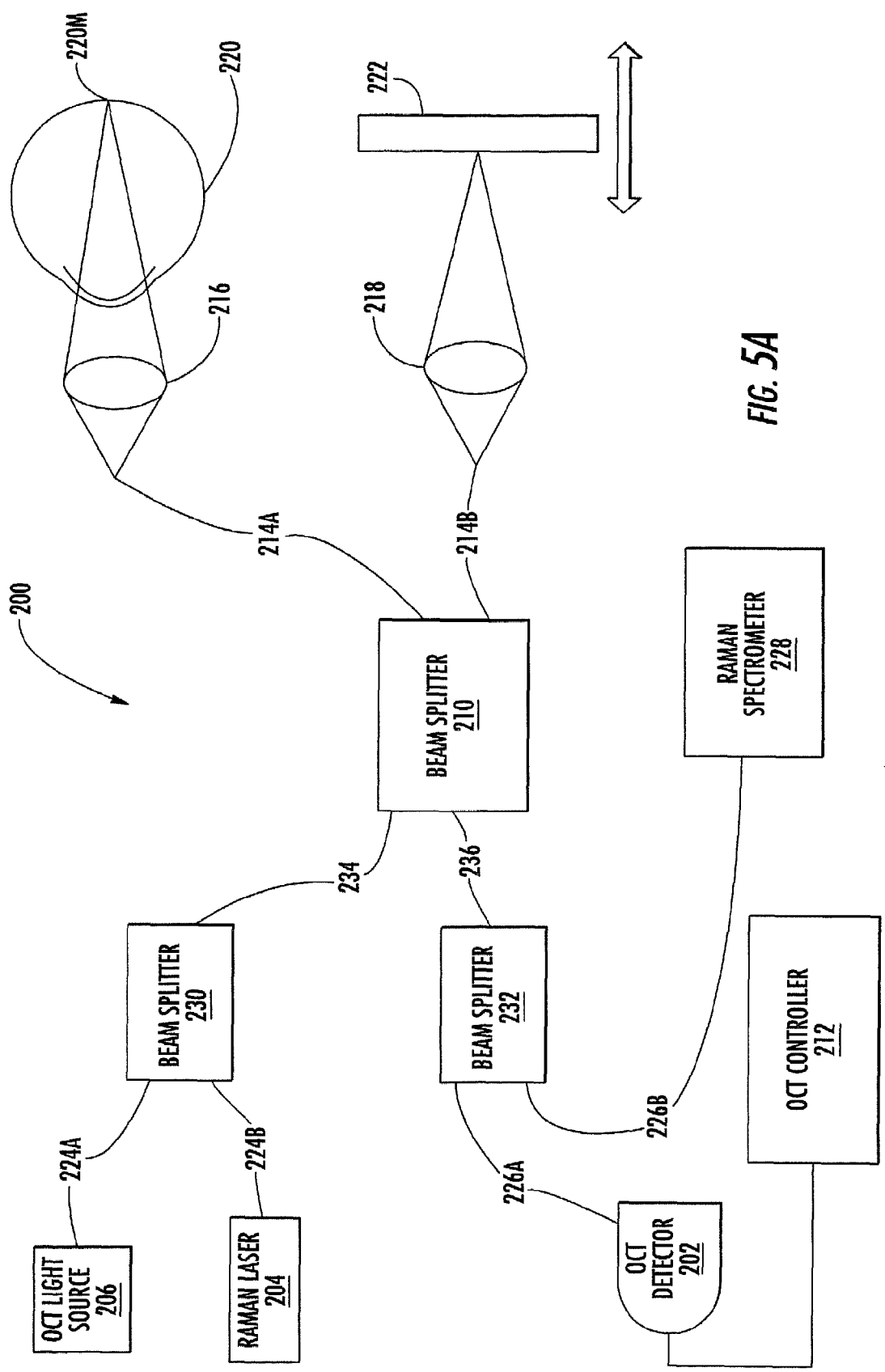
FIG. 5A-5B are a schematic diagrams of combination OCT/Raman spectrometer devices for measuring carotenoids in vivo according to embodiments of the present invention.

Referring to FIG. 5A, a combination OCT/Raman scattering system 200 includes an OCT light source 206 and a Raman laser 204. The OCT light source 206 can include a blue and/or infrared light source, such as a diode, as described with respect to the embodiments of FIG. 4. Excitation beams from the OCT light source 206 and/or the Raman laser 204 can be transmitted via fiber optic cables 224A and 224B, respectively, to a beam splitter 230, which is connected to another beam splitter 210 by fiber optic cable 234. The excitation beam(s) can be transmitted via a fiber optic cable 214A and a lens 216 to a macula 220M of an eye 220. The excitation beam from the OCT light source 206 can also be transmitted via a fiber optic cable 214B and a lens 218 to a reference mirror 222 to provide a reference beam similar to the reference beam described with respect to FIG. 4. An OCT detector 202 and an OCT controller 212 is connected to another beam splitter 232 by a fiber optic cable 226A, and a Raman spectrometer 228 is connected to the beam splitter 232 by a fiber optic cable 226B. The beam splitter 232 is connected to the beam splitter 210 by a fiber optic cable 236. The OCT controller 212 can analyze the interference spectra from the eye 220 and the reference mirror 222 at various depth levels as described with respect to the controller 110 in FIG. 4.

As illustrated in FIG. 5A, excitation beams can be transmitted to the eye 220 from the OCT light source 206 and the Raman laser 204 simultaneously in a single scan or, alternatively, in two separate scans: one scan for collecting OCT spectra and one scan for collecting Raman spectra. In some embodiments, the OCT light source 206 is an infrared diode that can provide detailed imaging information of the eye 220. The Raman spectra from the Raman spectrometer 228 can be used to provide carotenoid concentrations in the same region by identifying the characteristic Raman spectrum of carotenoids from the collected Raman spectra from the eye 220. The Raman spectra can be combined with imaging information from the OCT scan, e.g., by "overlaying" the Raman spectra with the OCT image.

In some embodiments, the OCT light source 206 is a blue diode that can provide both imaging information and carotenoid level information using the techniques described herein, e.g., such as the techniques described with respect to FIGS. 3 and 4. The Raman spectra can be combined with the imaging and/or carotenoid levels from the OCT scan to provide enhanced carotenoid level information, such as information at multiple depth layers in the macula 220M of the eye 220.

In some embodiments, a blue diode excitation beam, an infrared diode excitation beam, a Raman laser excitation beam or a combination thereof can be provided substantially simultaneously. The resulting reemitted light from the macula 220M can be obtained and filtered and/or analyzed to provide Raman spectra and/or OCT spectra information indicating various carotenoid levels and/or OCT imaging information. In other embodiments, a blue diode excitation beam, an infrared diode excitation beam, and/or a Raman laser excitation beam can be used during separate OCT or Raman scans to provide separate Raman and OCT information that can be subsequently combined to provide the spatial representation of carotenoid levels in the retina.

The Raman laser 204 can transmit an excitation beam selected to generate a resonant Raman spectrum for at least one of the carotenoids in the retina. For example, the Raman laser 204 can transmit light at a wavelength between about 400 and 530 nm. In some embodiments, light sources, such as a Raman laser and/or a blue low coherent light source, and/or a Raman spectrometer can be added to a convention OCT scanning device, which typically includes an infrared light source. These components can be added to conventional OCT scanning devices as modular components on existing devices. Conventional OCT scanning devices are commercially available from Carl Zeiss Meditec, Inc 5160 Hacienda Dr, Dublin, Calif. (U.S.A.).

Figure 5B:
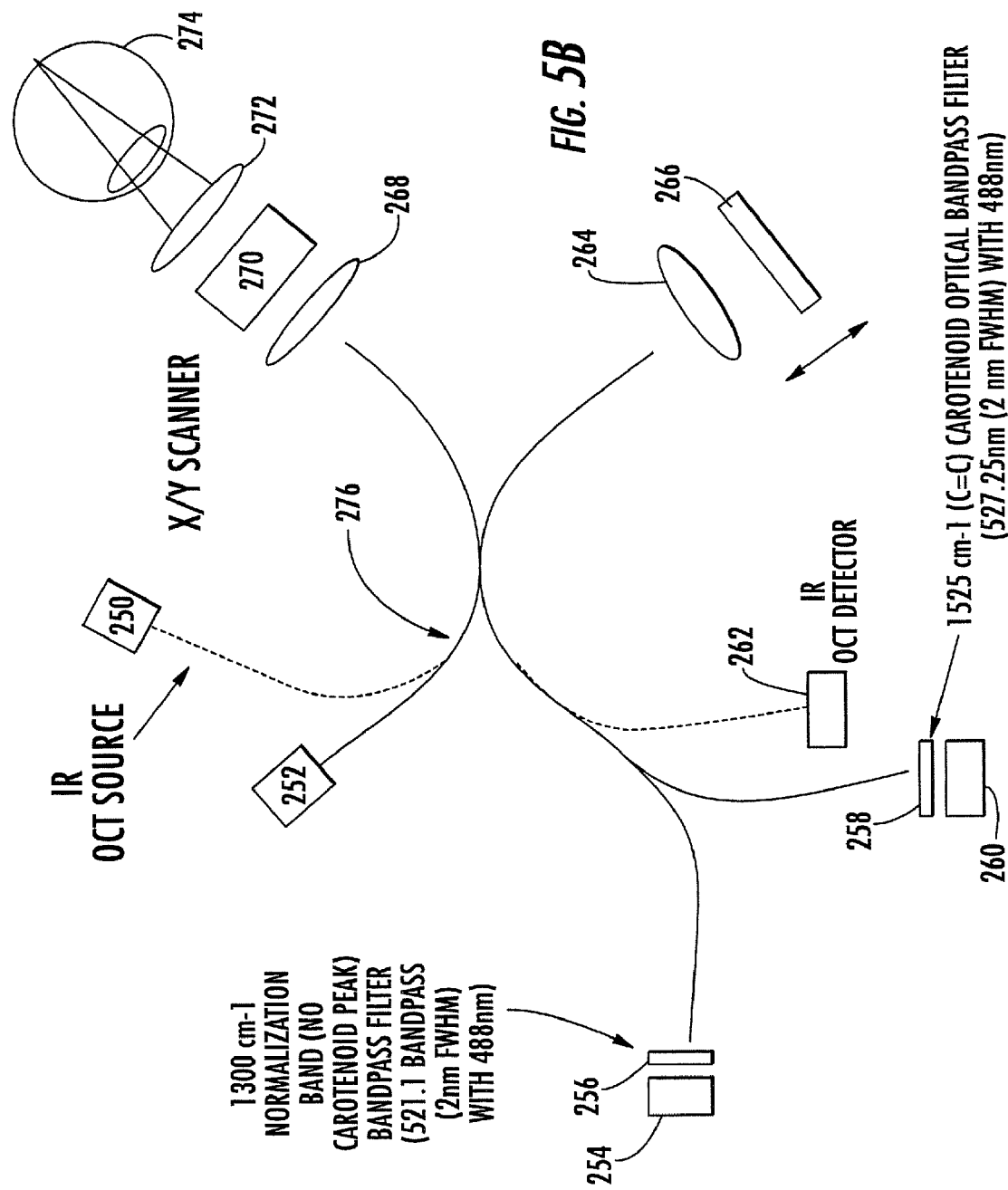

For example, as illustrated in FIG. 5B, a conventional OCT scanning device can include an infrared low coherent light source 250, an infrared OCT detector 262, a reference lens 264, a reference mirror 266, scanning lenses 268, 272, and an "X/Y" cross sectional scanner 270 that is configured to perform an OCT scan of an eye 274. The components that can be added to the OCT scanning device include a blue light source 252 and bandpass filters 256, 258 connected to detectors 254, 260, respectively. The components of the OCT scanning device shown are connected as illustrated in FIG. 5B by fiber optic cables 276. The blue light source 252 can be a low coherent light source, such as a blue superluminescent diode, or the blue light source 252 can be a blue laser. The blue light source 252 can be configured to provide a Raman excitation beam to the eye 274.

In some embodiments, the blue light source 252 can produce resonant Raman scattered light from macular carotenoids at 1008, 1159, and 1525 $cm^{-1}$ wavenumbers. For example, using a source excitation wavelength of 488 nm, a 1525 $cm^{-1}$ carotenoid Raman peak can occur at 527.25 nm. As illustrated in FIG. 5B, this peak can be detected by detector 260 using the optical bandpass filter 258 (e.g., a bandpass filter having a width of 2 nm). This peak can be compared to scattered light at a wavelength where resonant Raman scattering due to the presence of carotenoids is not expected, such as at 521.1 nm (corresponding to a wavenumber of 1300 $cm^{-1}$). This scattered light can be detected by detector 254 using the optical bandpass filter 256. The ratio of these two values as a function of the position of the cross sectional scanner 270 may be used to map carotenoid levels across the retina. The blue light source 252 may be switched off, and the infrared OCT light source 250, which can be supplied with a conventional OCT scanner, may be used to provide an OCT scan of the eye. Alternatively, the blue light source 252 and the infrared light source 250 can be used substantially simultaneously. The carotenoid levels can be detected using spectral information from the blue light source 252, including resonant Raman spectra, and the carotenoid levels can be mapped onto structural features of the retina revealed using an infrared OCT scan with infrared light source 250.

Figure 6:
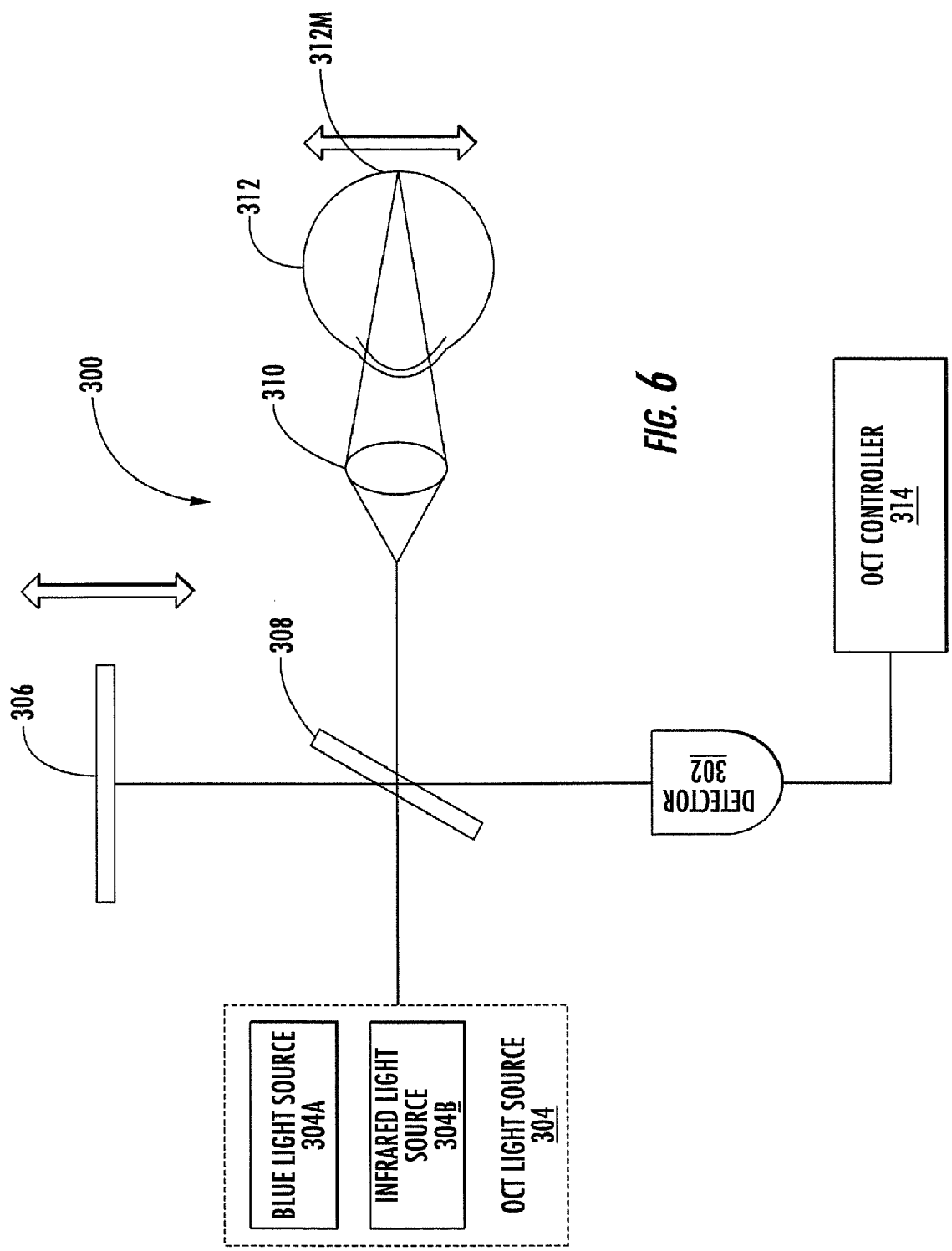
FIG. 6 is a schematic diagram of an OCT device for measuring carotenoids in vivo according to embodiments of the present invention.

Further embodiments of an OCT scanning system 300 are shown in FIG. 6. As illustrated, the OCT scanning system 300 includes an OCT excitation light source 304 having a blue light source 304A and/or an infrared light source 304B. An excitation beam is transmitted from the light source 304 through a beam splitter 308 to a lens 310 that focuses the light on a macula 312M of an eye 312. The beam splitter 308 also transmits the excitation beam to a reference mirror 306. The light that is reemitted from the reference mirror 306 and the eye 312 is detected by a detector 302 and processed by an OCT controller 314. The configuration shown in FIG. 6 is generally referred to as a Michelson interferometry configuration. The reference mirror 306 can be moved towards and away from the beam splitter 308 to provide depth information to the controller 314. The excitation beam through the lens 310 can be moved in a traverse direction to provide a cross-sectional scan of the eye 312. The controller 314 can analyze the resulting interference signal and the OCT absorption and/or reflectance spectra to provide one or more cross sectional spatial representations of carotenoid levels in the macula 312M of the eye 312.

Figure 7:
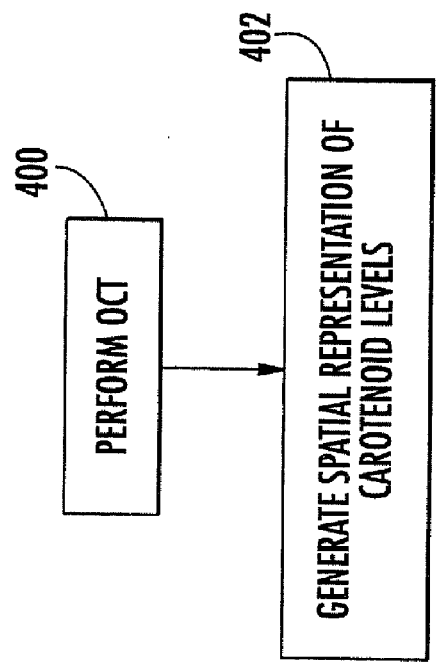

Operations that can be performed by the systems described herein are shown in FIG. 7. An OCT scan can be performed on a retina of a subject at Block 400. The OCT scan can be used to generate a spatial representation of carotenoid levels in the retina at Block 402. For example, a wavelet transformation and/or a Fourier transformation can be applied to the OCT signal to obtain spectral data. The spectral data and the intensity of the OCT signal can be used to generate structural and spectral data for spatial points in the retina. A characteristic absorption and/or reflectance spectra for carotenoids can be identified. For example, the spectral data can be analyzed using various mathematical techniques, including Fourier transforms and wavelet transforms. As another example, ratios of wavelengths can be examined to determine carotenoid levels. Chemometrics and/or pulsed oximetry techniques can also be used. The identified characteristic absorption and/or reflectance spectra can also be characteristic of the concentration of carotenoids in the retina. The concentrations of carotenoids can then be mapped in a two- and/or and three-dimensional morphology spatial representation of the target regions of the eye.

Figure 8:
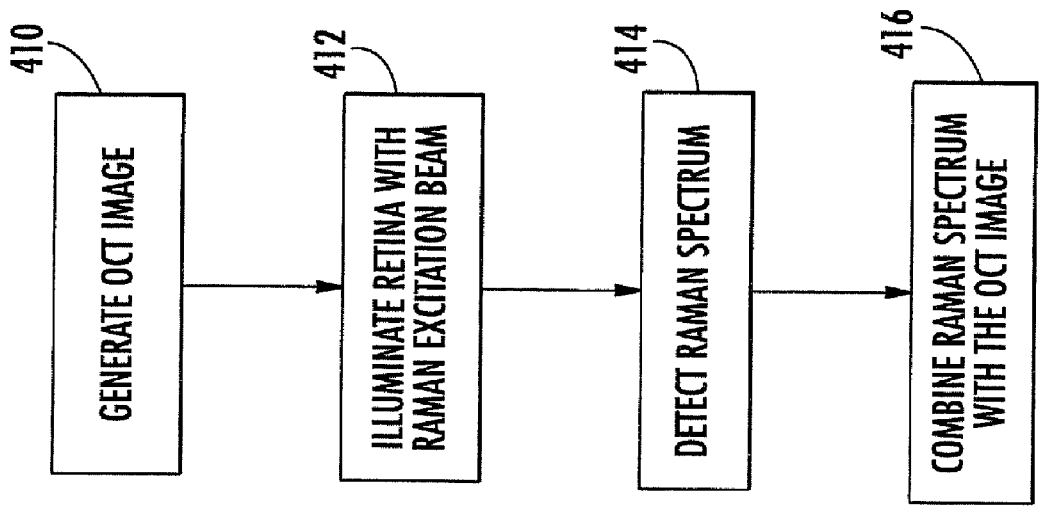
FIGS. 7 and 8 are flowcharts illustrating operations according to embodiments of the present invention.

Further operations that can be performed by the systems described herein are shown in FIG. 8. An OCT image is generated at Block 410. The retina is illuminated with a Raman optical excitation beam having a wavelength selected to generate a resonant Raman spectrum of at least one of the carotenoids at Block 412. A resonant Raman spectrum corresponding to the retina is detected at Block 414. The detected Raman spectrum is combined with the OCT image of the retina to generate a spatial representation of carotenoid levels that may be present in the retina at Block 416.

Although embodiments of the present invention have been described herein with reference to ocular OCT scans on the retina or macula, it should be understood that the methods and systems described herein may be applied to other areas of the body. More particularly, minimally invasive in vivo methods for assessing carotenoids in a tissue of interest can include performing OCT on a selected tissue of interest of a subject. The selected tissue can include the skin or internal organs, such as the bladder and prostate. A spatial representation of carotenoid levels in the selected tissue can be generated based on data from the OCT of the region using the techniques described herein.

For example, OCT scan of other tissue can be made using non-invasive or minimally invasive techniques, including techniques using probes, such as those described in U.S. Pat. No. 6,564,087, the disclosure of which is hereby incorporated by reference in its entirety. OCT scanning probes can be inserted directly into a tissue or organ through a tissue wall and/or into a natural lumen of a hollow organ or space (such as into a sinus cavity, a blood vessel, or other body cavity).

Carotenoids in other areas of the body include carotenoids that absorb blue, yellow, red, green or other wavelengths of light. For example, lycopene is typically red in color. Appropriate OCT excitation light sources can be based on the carotenoid of interest, the selection of which would be known to those of skill in the art. For example, the OCT light source used can be selected so that some of the excitation wavelengths are absorbed by carotenoids of interest.

OCT scans of organs, such as the bladder and prostate, can be used to evaluate carotenoid levels therein. The overall health of tissue and/or the efficacy of various types of treatment can also be assessed. Spatial representations of carotenoid levels in the tissue can be obtained before and/or after a treatment is administered. Embodiments of the present invention may also be used to evaluate, adjust and/or identify a suitable dose of a selected treatment based on the carotenoid levels.

Additionally, as noted above, while embodiments of the present invention are described herein with reference to carotenoids, it should be understood that levels of other substances may also be detected. In particular, the techniques described herein may also be used to generate a spatial representation of retinoid levels in a selected tissue of a subject based on data from an OCT scan of the tissue region. For example, retinoids may also be detected using data from an OCT scan of an area of the retina using an OCT light source selected to provide an absorption and/or reflectance spectrum an/or a Raman scattering spectrum. The wavelengths of the excitation light source can be selected based on the absorption or Raman scattering characteristics of the retinoid of interest. For example, the excitation light source can emit wavelengths between about 400 and about 450 nm. Retinoid levels may be assessed, for example, in the treatment or assessment of ocular conditions, such as retinitis pigmentosa.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. Therefore, it is to be understood that the foregoing is illustrative of the present invention and is not to be construed as limited to the specific embodiments disclosed, and that modifications to the disclosed embodiments, as well as other embodiments, are intended to be included within the scope of the appended claims. The invention is defined by the following claims, with equivalents of the claims to be included therein.

That which is claimed is:

1. A non-invasive in vivo method for assessing carotenoids in the retina and/or macula, comprising:
    performing Optical Coherence Tomography (OCT) on a retina of a subject to obtain absorption and/or reflectance spectral data correlated with carotenoid levels; and
    generating a spatial representation of carotenoid levels in the retina based on comparing the spectral data from the OCT of the retina with a priori reference spectra.

2. A method according to claim 1, wherein the performing step comprises transmitting a blue excitation light to the retina.

3. A method according to claim 1, wherein the performing step comprises transmitting an excitation light comprising a blue excitation light and an infrared excitation light.

4. A method according to claim 1, wherein the generating step comprises applying a wavelet transformation to an OCT signal to generate spectral data of the retina.

5. A method according to claim 1, wherein the performing step comprises transmitting a low coherence light with a superluminescent diode.

6. A method according to claim 1, wherein the generating step comprises repeating the performing and generating steps after administration of a selected treatment to provide a first and second spatial representation of carotenoid levels in the retina.

7. A method according to claim 6, further comprising comparing the first spatial representation with the second spatial representation and evaluating the efficacy of the selected treatment on age related macular degeneration (AMD) based on the comparing step.

8. A method according to claim 1, wherein the carotenoids include at least one of β-carotene, lutein, lycopene, xanthophyl, xanthophyll, and/or zeaxanthin.

9. A method according to claim 1, wherein carotenoids of interest have a chemical structure having at least one alternating double carbon-carbon bonds and/or single carbon-carbon bonds.

10. A method according to claim 1, wherein the a priori reference spectra corresponds to a plurality of different known concentrations of the carotenoids.

11. A method according to claim 1, wherein the generating step is able to determine a retinoid concentration level in the retina.

12. A method according to claim 1, further comprising detecting a resonant Raman spectra based on the OCT data.

13. A method according to claim 1, wherein the performing step comprises:
    scanning the retina with low coherence light of an OCT scanner;

detecting reemitted light from the retina in response thereto;

interfering the detected light from the retina with a reference light beam to provide an interference signal; and obtaining the spectral data from the interference signal.

14. A method according to claim 1, wherein the performing step comprises detecting reflectance and/or absorption spectra of different layers of the retina.

15. A method according to claim 14, wherein the different layers includes at least seven layers.

16. A method according to claim 1, wherein the generating step comprises generating a two-dimensional map of carotenoid levels in a cross-sectional spatial representation of the retina from the OCT.

17. A method according to claim 1, wherein the generating step comprises generating a three-dimensional morphology map of carotenoid levels in the retina.

18. A method according to claim 1, wherein the spatial representation comprises a map of a plurality of adjacent layers of the retina and covers a region about 2-5 mm wide.

19. A method according to claim 1, wherein the spatial representation comprises at least about 1000 data pixels.

20. A method according to claim 1, wherein the generating step comprises generating an intensity graduated and/or color indexed image of different levels of carotenoids in the retina.

21. A method according to claim 1, further comprising assessing age-related macular degeneration (AMD) based on the spatial representation of the carotenoid levels.

22. A method according to claim 1, wherein the performing step comprising performing OCT on the macular portion of the retina.

23. A method according to claim 1, wherein the performing step comprises transmitting a low coherence light to a portion of the retina.

24. A non-invasive in vivo method for assessing carotenoids in the retina and/or macula, comprising:

performing Optical Coherence Tomography (OCT) on a retina of a subject to obtain spectral data correlated with carotenoid levels; and generating a spatial representation of carotenoid levels in the retina based on comparing the spectral data from the OCT of the retina with a priori reference spectra, the method further comprising:

illuminating a portion of the retina with an optical excitation beam having a wavelength selected to generate a resonant Raman spectrum of at least one of the carotenoid;

detecting a resonant Raman spectrum corresponding to the selected illuminated region of the eye; and combining resonant Raman spectrum data with OCT data to generate the spatial representation of carotenoid levels in the retina.

25. A method according to claim 24, wherein the generating and illuminating steps are performed substantially simultaneously.

26. A method according to claim 25, wherein the generating step further comprises filtering the resonant Raman spectrum from the OCT spectral data.

* * * * *

UNITED STATES PATENT AND TRADEMARK OFFICE
CERTIFICATE OF CORRECTION

PATENT NO.        : 7,593,763 B2
APPLICATION NO.   : 10/773099
DATED             : September 22, 2009
INVENTOR(S)       : Lambert et al.

Page 1 of 1

It is certified that error appears in the above-identified patent and that said Letters Patent is hereby corrected as shown below:

Column 16, Claim 24, Lines 16-17: Please correct "one of the carotenoid;" to read -- one of the carotenoids; --

Signed and Sealed this

First Day of December, 2009

David J. Kappos
*Director of the United States Patent and Trademark Office*

UNITED STATES PATENT AND TRADEMARK OFFICE
CERTIFICATE OF CORRECTION

PATENT NO.       : 7,593,763 B2                                             Page 1 of 1
APPLICATION NO.  : 10/773099
DATED            : September 22, 2009
INVENTOR(S)      : Lambert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1569 days.

Signed and Sealed this

Twenty-eighth Day of September, 2010

David J. Kappos
*Director of the United States Patent and Trademark Office*